United States Patent
Cohn et al.

(10) Patent No.: US 6,890,353 B2
(45) Date of Patent: May 10, 2005

(54) METHOD AND APPARATUS FOR REDUCING MITRAL REGURGITATION

(75) Inventors: William E. Cohn, Chestnut Hill, MA (US); John R. Liddicoat, Sewickley, PA (US); Richard B. Streeter, Winchester, MA (US); Daniel C. Taylor, Brighton, MA (US); Steven B. Woolfson, Boston, MA (US)

(73) Assignee: Viacor, Inc., Wilmington, MA (US)

( * ) Notice: Subject to any disclaimer, the term of this patent is extended or adjusted under 35 U.S.C. 154(b) by 0 days.

(21) Appl. No.: 10/104,720

(22) Filed: Mar. 22, 2002

(65) Prior Publication Data

US 2002/0183841 A1 Dec. 5, 2002

Related U.S. Application Data

(63) Continuation-in-part of application No. 10/090,968, filed on Mar. 5, 2002, which is a continuation-in-part of application No. 10/068,264, filed on Feb. 5, 2002, now Pat. No. 6,656,221, and a continuation-in-part of application No. 10/068,700, filed on Feb. 5, 2002, now Pat. No. 6,790,231.

(60) Provisional application No. 60/278,153, filed on Mar. 23, 2001, provisional application No. 60/279,974, filed on Mar. 29, 2001, provisional application No. 60/280,038, filed on Mar. 30, 2001, provisional application No. 60/279,973, filed on Mar. 29, 2001, provisional application No. 60/283,820, filed on Apr. 13, 2001, provisional application No. 60/312,217, filed on Aug. 14, 2001, provisional application No. 60/339,481, filed on Oct. 26, 2001, and provisional application No. 60/348,424, filed on Jan. 14, 2002.

(51) Int. Cl.$^7$ .................................................. A61F 2/24

(52) U.S. Cl. ...................................... 623/2.37; 623/903

(58) Field of Search ................................ 606/151, 220, 606/232, 213; 128/898; 623/1.15, 903, 2.36, 2.37

(56) References Cited

U.S. PATENT DOCUMENTS

| | | | |
|---|---|---|---|
| 4,669,473 A | 6/1987 | Richards et al. | |
| 4,917,698 A | 4/1990 | Carpentier et al. | |
| 4,944,745 A | 7/1990 | Sogard et al. | |

(Continued)

FOREIGN PATENT DOCUMENTS

| | | | |
|---|---|---|---|
| EP | 0756853 A1 | 2/1997 | |
| JP | 409322936 A | 12/1997 | |
| WO | WO 01/00111 A1 | 1/2001 | |
| WO | WO 01/54618 A1 | 8/2001 | |
| WO | WO 02/053206 A2 | 7/2002 | |
| WO | WO 02/060352 A1 | 8/2002 | |
| WO | WO 02/062270 A1 | 8/2002 | |
| WO | WO 02/091908 A2 | 11/2002 | |
| WO | WO 02/100240 A2 | 12/2002 | |
| WO | WO 03/037171 A2 | 5/2003 | |

OTHER PUBLICATIONS

Buchanan, James W., Circumferential Suture of the Mitral Annulus for Correction of Mitral Regurgitation in Dogs, Veterinary Surgery, 1998, pp. 182–193.

Kerstetter, Kyle K. et al., Short–Term Hemodynamic Evaluation of Circumferential Mitral Annuloplasty for Correction of Mitral Valve Regurgitation in Dogs, Veterinary Surgery, 1998, pp. 216–223.

Beardow, Andrew W. et al., Chronic Mitral Valve Disease in Cavalier King Charles Spaniels: 95 Cases (1987–1991), JAVMA vol. 203, No. 7, Oct. 1, 1993, pp. 1023–1029.

(Continued)

*Primary Examiner*—Brian E Pellegrino
(74) *Attorney, Agent, or Firm*—Pandiscio & Pandiscio

(57) ABSTRACT

Apparatus for reducing mitral regurgitation, by applying a force to the wall of the coronary sinus so as to force the posterior leaflet anteriorly and thereby reduce mitral regurgitation.

11 Claims, 14 Drawing Sheets

U.S. PATENT DOCUMENTS

| | | | |
|---|---|---|---|
| 5,061,277 A | 10/1991 | Carpentier et al. | |
| 5,092,889 A | 3/1992 | Campbell, Jr. | |
| 5,269,809 A | 12/1993 | Hayhurst et al. | |
| 5,332,402 A | 7/1994 | Teitelbaum | |
| 5,383,892 A | 1/1995 | Cardon et al. | |
| 5,389,091 A | 2/1995 | Moorehead | |
| 5,443,481 A | * 8/1995 | Lee | 606/213 |
| 5,476,506 A | 12/1995 | Lunn | |
| 5,545,209 A | 8/1996 | Roberts et al. | |
| 5,569,198 A | 10/1996 | Racchini | |
| 5,569,201 A | 10/1996 | Burns | |
| 5,575,799 A | 11/1996 | Bolanos et al. | |
| 5,720,726 A | 2/1998 | Marcadis et al. | |
| 5,755,778 A | 5/1998 | Kleshinski | |
| 5,755,781 A | 5/1998 | Jayaraman | |
| 5,800,495 A | 9/1998 | Machek et al. | |
| 5,800,526 A | 9/1998 | Anderson et al. | |
| 5,855,565 A | 1/1999 | Bar-Cohen et al. | |
| 5,957,949 A | 9/1999 | Leonhardt et al. | |
| 5,980,570 A | 11/1999 | Simpson | |
| 5,984,917 A | 11/1999 | Fleischman et al. | |
| 6,033,436 A | * 3/2000 | Steinke et al. | 623/1.15 |
| 6,051,020 A | 4/2000 | Goicoechea et al. | |
| 6,071,263 A | 6/2000 | Kirkman | |
| 6,086,599 A | 7/2000 | Lee et al. | |
| 6,090,136 A | 7/2000 | McDonald et al. | |
| 6,119,037 A | 9/2000 | Kellogg et al. | |
| 6,162,245 A | 12/2000 | Jayaraman | |
| 6,165,194 A | 12/2000 | Denardo | |
| 6,187,040 B1 | 2/2001 | Wright | |
| 6,210,432 B1 | 4/2001 | Solem et al. | |
| 6,241,746 B1 | 6/2001 | Bosma et al. | |
| 6,258,117 B1 | 7/2001 | Camrud et al. | |
| 6,277,107 B1 | 8/2001 | Lurie et al. | |
| 6,328,765 B1 | * 12/2001 | Hardwick et al. | 623/23.76 |
| 6,332,896 B1 | 12/2001 | Hubbard et al. | |
| 6,402,781 B1 | 6/2002 | Langberg et al. | |
| 6,419,696 B1 | 7/2002 | Ortiz et al. | |
| 6,537,314 B2 | 3/2003 | Langberg et al. | |
| 6,585,716 B2 | 7/2003 | Altman | |
| 6,602,288 B1 | 8/2003 | Cosgrove et al. | |
| 6,656,221 B2 | 12/2003 | Taylor et al. | |
| 2001/0018611 A1 | 8/2001 | Solem et al. | |
| 2001/0044568 A1 | 11/2001 | Langberg et al. | |
| 2001/0052345 A1 | 12/2001 | Niazi | |
| 2002/0016628 A1 | 2/2002 | Langberg et al. | |
| 2002/0087173 A1 | 7/2002 | Alferness et al. | |
| 2002/0103532 A1 | 8/2002 | Langberg et al. | |
| 2002/0103533 A1 | 8/2002 | Langberg et al. | |
| 2002/0151961 A1 | 10/2002 | Lashinsi et al. | |
| 2002/0169502 A1 | 11/2002 | Mathis | |
| 2002/0169504 A1 | 11/2002 | Alferness et al. | |
| 2003/0069636 A1 | 4/2003 | Solem et al. | |
| 2003/0083538 A1 | 5/2003 | Adams et al. | |
| 2003/0093148 A1 | 5/2003 | Bolling et al. | |
| 2003/0105520 A1 | 6/2003 | Alferness et al. | |

OTHER PUBLICATIONS

Davila, Julio C. et al., Circumferential Suture of The Mitral Ring, 18 pages.

Glover, Robert P. et al., The Treatment of Mitral Valve Insufficiency By The Purse–String Technique, The Journal of Thoracic Surgery, Jan. 1957, 14 pages.

Davila, Julio C. et al., Circumferential Suture of The Mitral Valve for the Correction of Regurgitation, The American Journal of Cardiology, Inc., Sep. 1958, 6 pages.

Buchanan, James W., Causes and Prevalence of Cardiovascular Disease, Current Veterinary Therapy XI, WB Saunders Co., 1992, 2 pages.

* cited by examiner

METHOD AND APPARATUS FOR REDUCING MITRAL REGURGITATION

REFERENCE TO PENDING PRIOR PATENT APPLICATIONS

This patent application:

(1) is a continuation-in-part of prior U.S. patent application Ser. No. 10/068,264, filed Feb. 5, 2002 now U.S. Pat. No. 6,656,221 by Daniel C. Taylor et al. for METHOD AND APPARATUS FOR IMPROVING MITRAL VALVE FUNCTION;

(2) is a continuation-in-part of prior U.S. patent application Ser. No. 10/068,700, filed Feb. 5, 2002 now U.S. Pat. No. 6,790,231 by William E. Cohn et al. for APPARATUS AND METHOD FOR REDUCING MITRAL REGURGITATION;

(3) is a continuation-in-part of prior U.S. patent application Ser. No. 10/090,968, filed Mar. 5, 2002 by William E. Cohn et al. for APPARATUS AND METHOD FOR REDUCING MITRAL REGURGITATION;

(4) claims benefit of prior U.S. Provisional Patent Application Ser. No. 60/278,153, filed Mar. 23, 2001 by William E. Cohn et al. for METHOD AND APPARATUS TO IMPROVE MITRAL VALVE FUNCTION;

(5) claims benefit of prior U.S. Provisional Patent Application Ser. No. 60/279,974, filed Mar. 29, 2001 by Daniel C. Taylor et al. for METHOD AND APPARATUS TO IMPROVE MITRAL VALVE FUNCTION;

(6) claims benefit of prior U.S. Provisional Patent Application Ser. No. 60/280,038, filed Mar. 30, 2001 by William E. Cohn et al. for METHODS AND APPARATUS FOR TEMPORARY IMPROVEMENT IN MITRAL VALVE FUNCTION;

(7) claims benefit of prior U.S. Provisional Patent Application Ser. No. 60/279,973, filed Mar. 29, 2001 by Daniel C. Taylor et al. for METHODS AND DEVICES TO IMPROVE MITRAL VALVE FUNCTION;

(8) claims benefit of prior U.S. Provisional Patent Application Ser. No. 60/283,820, filed Apr. 13, 2001 by William E. Cohn et al. for METHOD AND APPARATUS FOR TEMPORARY IMPROVEMENT IN MITRAL VALVE FUNCTION;

(9) claims benefit of prior U.S. Provisional Patent Application Ser. No. 60/312,217, filed Aug. 14, 2001 by Daniel C. Taylor et al. for METHOD AND APPARATUS FOR TEMPORARY IMPROVEMENT IN MITRAL VALVE FUNCTION;

(10) claims benefit of prior U.S. Provisional Patent Application Ser. No. 60/339,481, filed Oct. 26, 2001 by William E. Cohn et al. for TRANSVASCULAR APPROACH TO MITRAL VALVE PROCEDURES; and

(11) claims benefit of prior U.S. Provisional Patent Application Ser. No. 60/348,424, filed Jan. 14, 2002 by Daniel C. Taylor et al. for METHOD AND APPARATUS TO IMPROVE MITRAL VALVE FUNCTION;

The aforementioned eleven (11) patent applications are hereby incorporated herein by reference.

FIELD OF THE INVENTION

This invention relates to surgical methods and apparatus in general, and more particularly to surgical methods and apparatus for improving mitral valve function.

BACKGROUND OF THE INVENTION

Mitral valve repair is the procedure of choice to correct mitral regurgitation of all etiologies. With the use of current surgical techniques, between 70% and 95% of regurgitant mitral valves can be repaired. The advantages of mitral valve repair over mitral valve replacement are well documented. These include better preservation of cardiac function and reduced risk of anticoagulant-related hemorrhage, thromboembolism and endocarditis.

In current practice, mitral valve surgery requires an extremely invasive approach that includes a chest wall incision, cardiopulmonary bypass, cardiac and pulmonary arrest, and an incision on the heart itself to gain access to the mitral valve. Such a procedure is associated with high morbidity and mortality. Due to the risks associated with this procedure, many of the sickest patients are denied the potential benefits of surgical correction of mitral regurgitation. In addition, patients with moderate, symptomatic mitral regurgitation are denied early intervention and undergo surgical correction only after the development of cardiac dysfunction.

Mitral regurgitation is a common occurrence in patients with heart failure and a source of important morbidity and mortality in these patients. Mitral regurgitation in patients with heart failure is caused by changes in the geometric configurations of the left ventricle, papillary muscles and mitral annulus. These geometric alterations result in mitral leaflet tethering and incomplete coaptation at systole. In this situation, mitral regurgitation is corrected by plicating the mitral valve annulus, either by (i) sutures alone or by (ii) sutures in combination with a support ring, so as to reduce the circumference of the distended annulus and restore the original geometry of the mitral valve annulus.

More particularly, current surgical practice for mitral valve repair generally requires that the posterior mitral valve annulus be reduced in radius by surgically opening the left atrium and then fixing sutures, or sutures in combination with a support ring, to the internal surface of the annulus; this structure is used to pull the annulus back into a smaller radius, thereby reducing mitral regurgitation by improving leaflet coaptation.

This method of mitral valve repair, generally termed "annuloplasty", effectively reduces mitral regurgitation in heart failure patients. This, in turn, reduces symptoms of heart failure, improves quality of life and increases longetivity. Unfortunately, however, the invasive nature of mitral valve surgery and the attendant risks render most heart failure patients poor surgical candidates. Thus, a less invasive means to increase leaflet coaptation and thereby reduce mitral regurgitation in heart failure patients would make this therapy available to a much greater percentage of patients.

Mitral regurgitation also occurs in approximately 20% of patients suffering acute myocardial infarction. In addition, mitral regurgitation is the primary cause of cardiogenic shock in approximately 10% of patients who develop severe hemodynamic instability in the setting of acute myocardial infarction. Patients with mitral regurgitation and cardiogenic shock have about a 50% hospital mortality. Elimination of mitral regurgitation in these patients would be of significant benefit. Unfortunately, however, patients with acute mitral regurgitation complicating acute myocardial infarction are particularly high-risk surgical candidates, and are therefore not good candidates for a traditional annuloplasty procedure. Thus, a minimally invasive means to effect a temporary reduction or elimination of mitral regurgitation in these critically ill patients would afford them the time to recover from the myocardial infarction or other acute life-threatening events and make them better candidates for medical, interventional or surgical therapy.

A less invasive means to reduce mitral regurgitation would also be an attractive alternative for patients needing to undergo any of the following procedures: (a) isolated mitral valve repair, (b) multiple valve procedures, (c) mitral repair and coronary artery bypass, (d) mitral valve repair and other surgical procedure, or (e) mitral valve repair and an interventional cardiac procedure.

SUMMARY OF THE INVENTION

As a result, one object of the present invention is to provide a method and apparatus for treating mitral regurgitation which does not suffer from the disadvantages associated with conventional annuloplasty.

Another object of the present invention is to provide a method and apparatus for treating mitral regurgitation which can be deployed either permanently (e.g., for patients suffering from heart failure) or temporarily (e.g., for patients suffering from mitral regurgitation with acute myocardial infarction).

Another object of the present invention is to provide a minimally invasive method and apparatus for the repair of heart valves to improve their function.

Another object of the present invention is to provide a method and apparatus for the repair of the mitral valve that eliminates the need for cardiopulmonary bypass and/or cardiac arrest and/or general anesthesia.

Another object of the present invention is to provide a method and apparatus for the repair of the mitral valve that facilitates the use of smaller incisions.

Another object of the present invention is to provide a method and apparatus to effect a change in the geometry of the annulus of the mitral valve that increases mitral leaflet coaptation and reduces mitral valve regurgitation.

Another object of the present invention is to provide a method and apparatus to effect a change in the geometry of the left atrium that increases mitral leaflet coaptation and reduces mitral regurgitation.

Another object of the present invention is to provide an apparatus that is anchored partially or wholly outside the coronary sinus such that tension can be created between the proximal and distal anchored points so as to move these two points closer together and thereby effect a favorable change in the geometry of the mitral valve annulus.

Another object of the present invention is to provide an apparatus that is anchored partially or wholly outside the coronary sinus such that tension can be created between the proximal and distal anchored points so as to move these two points closer together and thereby effect a favorable change in left atrial geometry, with minimal, if any, trauma to the blood vessel.

Another object of the present invention is to provide a method and apparatus to alter the geometry of the mitral valve annulus such that (1) the distance between the anterior and posterior mitral leaflets is shortened; and (2) the coronary sinus assumes a more straight course.

Another object of the present invention is to provide a method and apparatus to alter left atrial geometry such that (1) the distance between the anterior and posterior mitral leaflets is shortened; and (2) the coronary sinus assumes a more straight course.

Another object of the present invention is to provide a method and apparatus for altering the geometry of the mitral valve annulus in an adjustable and/or reversible fashion such that the effect on mitral valve function can be adjusted so as to achieve the best possible result.

Another object of the present invention is to provide a method and apparatus for altering left atrial geometry in an adjustable and/or reversible fashion such that the effect on mitral valve function can be adjusted so as to achieve the best possible result.

Another object of the present invention is to provide an apparatus that is anchored partially or wholly outside the coronary sinus such that a greater geometric change in the left atrium can be created (that in turn increases mitral leaflet coaptation and reduces mitral regurgitation) when compared to anchoring only within the coronary sinus.

These and other objects are addressed by the present invention, which is made possible by the discovery that the mitral annulus may be remodeled without the plication of conventional, open-surgery annuloplasty.

The present invention comprises a method and apparatus for increasing mitral leaflet coaptation without direct surgical exposure of the mitral valve via the left atrium. More particularly, the present invention comprises a method and apparatus for effecting a geometric, conformational or dimensional alteration in the annulus of the mitral valve by manipulating cardiac structures external to the left atrium and, in so doing, improving mitral valve function.

In a preferred embodiment, the present invention utilizes access obtained in part via the coronary sinus. The coronary sinus is the largest vein of the heart. During a large portion of its course in the atrioventricular groove, the coronary sinus lies directly beneath the endocardium of the left atrium and adjacent to the posterior annulus of the mitral valve. An apparatus appropriately placed into the coronary sinus will be in direct apposition to the left atrium and the posterior annulus of the mitral valve. Manipulation of such apparatus may be used to effect a geometric change in the left atrium, and hence the annulus of the mitral valve, in order to increase mitral leaflet coaptation. Preferably, the apparatus is adjustable so that its effect may be varied, at the time of the initial procedure or at a later date, so as to achieve the best possible result.

In one preferred form of the invention, the apparatus comprises a distal anchor, a proximal anchor and a flexible filament extending therebetween. By setting the distal anchor distally, near the end of the coronary sinus, and setting the proximal anchor proximally, near the mouth of the coronary sinus, and thereafter adjustably cinching the filament between the two anchors, the geometry of the coronary sinus, and hence the geometry of the left atrium and the mitral valve, may be adjusted so as to improve mitral leaflet coaptation. The effects of this left atrial conformational change include (1) decreasing the distance between the anterior and posterior leaflets of the mitral valve; (2) straightening the posterior mitral valve annulus; and (3) decreasing the distance between the fibrous trigones of the heart by altering the shape of the mitral valve annulus.

Access to perform this procedure may be obtained either percutaneously via any vessel in the body or via a chamber of the heart, such as the right atrium. The latter approach may involve a chest wall incision or a thoracoscopic approach. Visualization of the procedure may be obtained by fluoroscopy, echocardiography, intravascular ultrasound, angioscopy, or real-time magnetic resonance imaging. It is anticipated that assessment of the efficacy of the procedure will be obtained with echocardiography, although other imaging modalities may also be suitable.

BRIEF DESCRIPTION OF THE DRAWINGS

The above and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

The coronary sinus is the largest vein in the human heart. During a large portion of its course in the atrioventricular groove, the coronary sinus typically extends adjacent to the left atrium of the heart for a distance of approximately 5 to 10 centimeters. Significantly, for a portion of its length, e.g., typically approximately 7–9 cm, the coronary sinus extends substantially adjacent to the posterior perimeter of the mitral annulus. The present invention takes advantage of this fact. More particularly, by deploying an appropriate apparatus in the coronary sinus, adjacent to the posterior leaflet of the mitral valve, pressure may be brought to bear on the posterior annulus of the mitral valve, whereby to move the posterior annulus anteriorly so as to improve leaflet coaptation and, as a result, reduce mitral regurgitation. In this respect it should be appreciated that the posterior annulus may be shifted anteriorly so as to achieve, or to attempt to achieve to the extent anatomically possible, leaflet-to-leaflet engagement or leaflet-to-annulus engagement (e.g., where a leaflet may be tethered due to left ventricular distortion). Both of these types of engagement, or targeted engagement, are intended to be encompassed by the terms "improved leaflet coaptation" and/or "increased leaflet coaptation" and the like.

In one preferred embodiment of the invention, access to the coronary sinus is gained percutaneously, e.g., the apparatus is introduced into the patient's vascular system via the jugular vein or via the left subclavian vein, passed down the superior vena cava, passed through the right atrium and then passed into the coronary sinus, where it is deployed. Alternatively, the apparatus may be introduced into the coronary sinus through a small incision in the heart, or through some other incision into the patient's vascular system.

Once deployed, the apparatus may be left in position permanently (e.g., in the case of patients suffering from mitral regurgitation associated with heart failure) or the elongated body may be left in position only temporarily (e.g., in the case of patients suffering from mitral regurgitation associated with acute myocardial infarction).

Visualization of the procedure may be obtained by fluoroscopy, echocardiography, intravascular ultrasound, angioscopy, real-time magnetic resonance imaging, etc. The efficacy of the procedure may be determined through echocardiography, although other imaging modalities may also be suitable.

Figure 1:
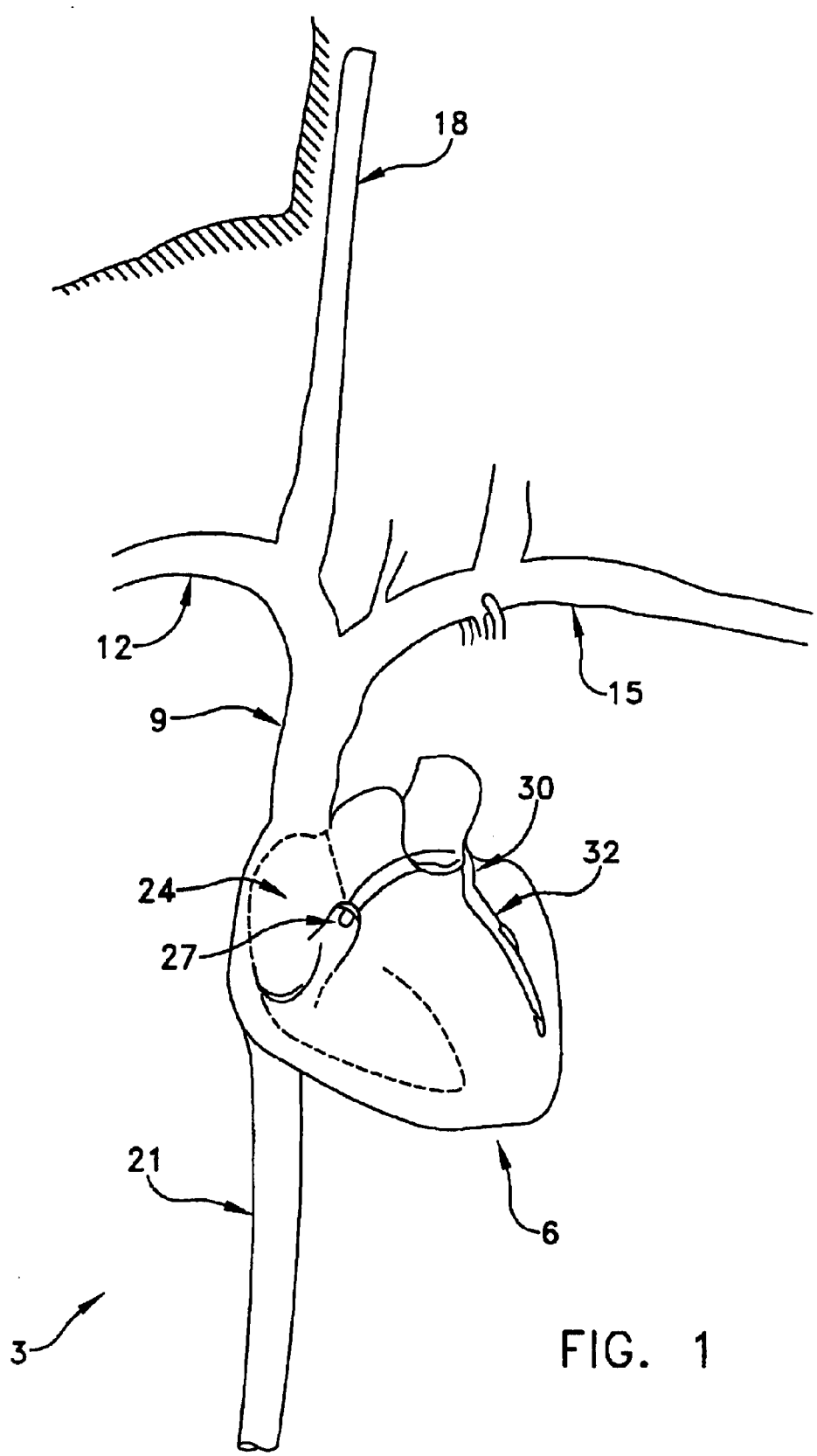
FIG. 1 is a schematic view of portions of the human vascular system.
Figure 2:
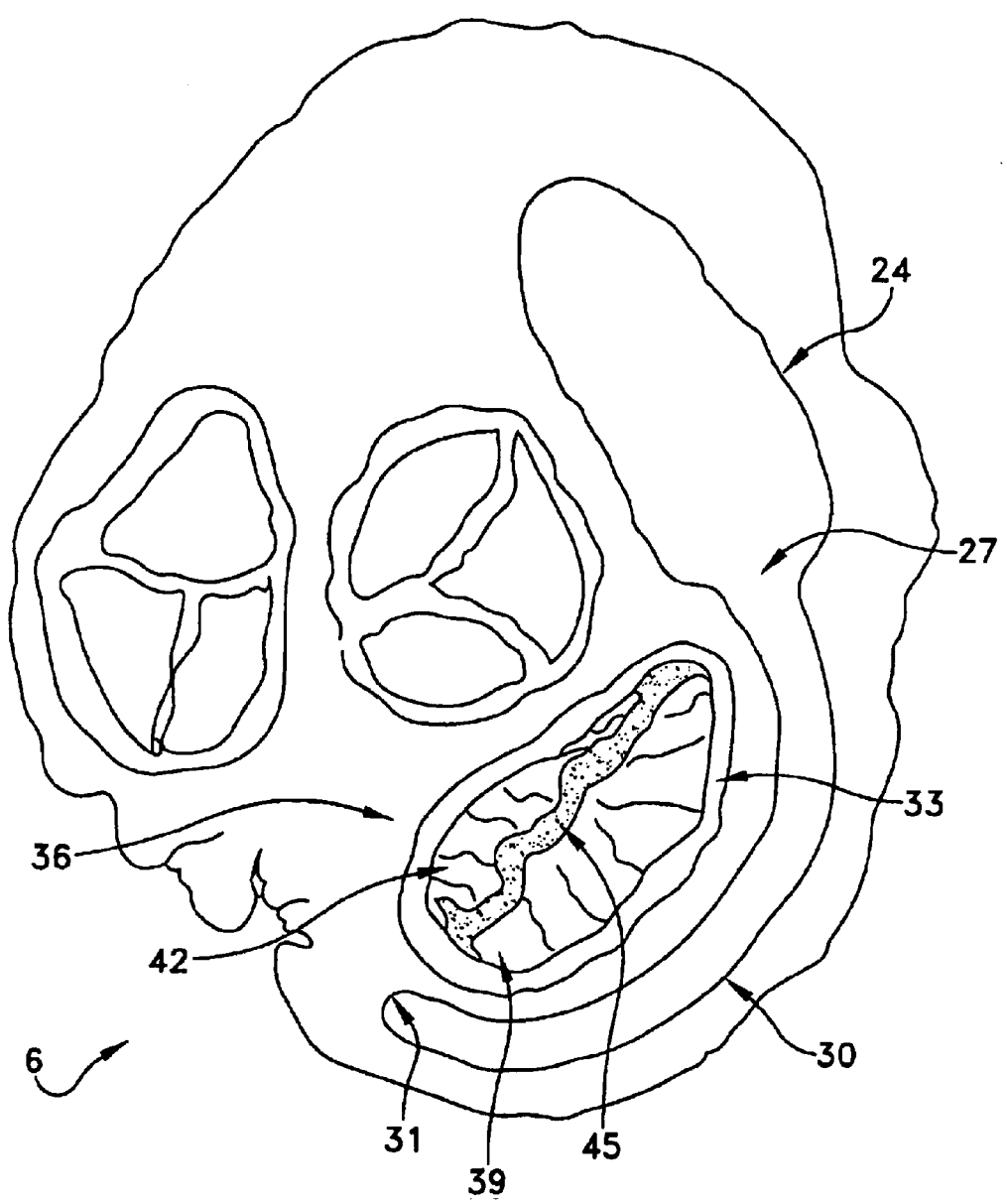
FIG. 2 is a schematic view of portions of the human heart.

Looking now at FIGS. 1 and 2, there are shown aspects of the cardiovascular system 3 of a patient. More particularly, cardiovascular system 3 generally comprises the heart 6, the superior vena cava 9, the right subclavian vein 12, the left subclavian vein 15, the jugular vein 18, and the inferior vena cava 21. Superior vena cava 9 and inferior vena cava 21 communicate with the heart's right atrium 24. The coronary ostium 27 leads to coronary sinus 30. At the far end 31 (FIG. 2) of coronary sinus 30, the vascular structure turns into the vertically-descending anterior interventricular vein ("AIV") 32 (FIG. 1). For purposes of the present invention, it can generally be convenient to consider the term "coronary sinus" to mean the vascular structure extending between coronary ostium 27 and AIV 32.

As seen in FIG. 2, between coronary ostium 27 and AIV 32, coronary sinus 30 generally extends substantially adjacent to the posterior perimeter of the annulus 33 of the mitral valve 36. Mitral valve 36 comprises a posterior leaflet 39 and an anterior leaflet 42. In the case of a regurgitant mitral valve, posterior leaflet 39 and anterior leaflet 42 will generally fail to properly coapt at systole, thereby leaving an intervening gap 45 which will permit regurgitation.

Figure 3:
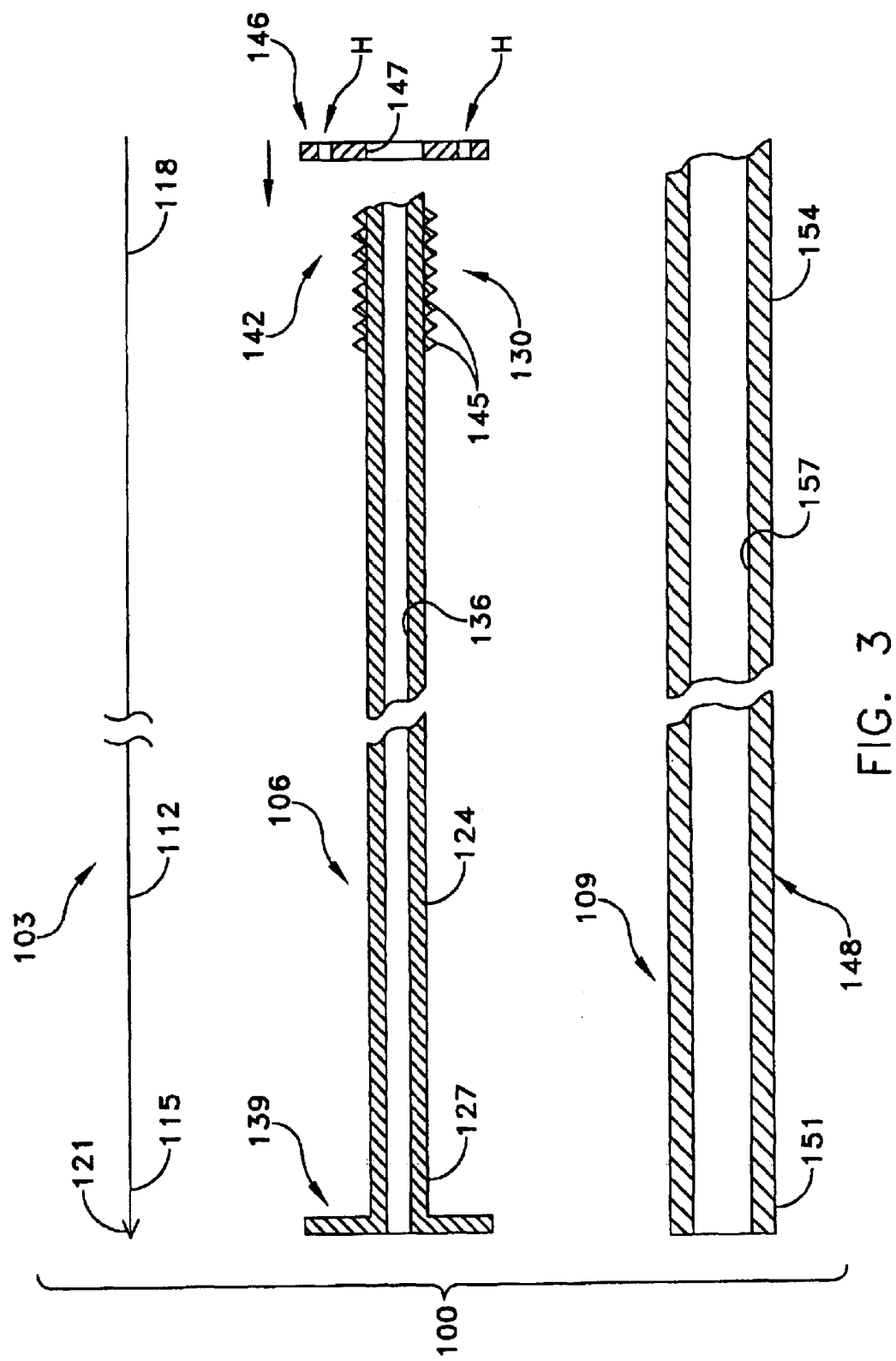
FIG. 3 is a schematic view showing one embodiment of apparatus formed in accordance with the present invention.

Looking next at FIG. 3, there is shown a system 100 which comprises one preferred embodiment of the present invention. More particularly, system 100 generally comprises a guidewire 103, a cinching device 106 and a delivery cannula 109.

Guidewire 103 comprises a flexible body 112 having a distal end 115 and a proximal end 118. The distal end 115 of guidewire 103 preferably includes a sharp tip 121 for allowing the distal end of guidewire 103 to penetrate tissue.

Figure 4:
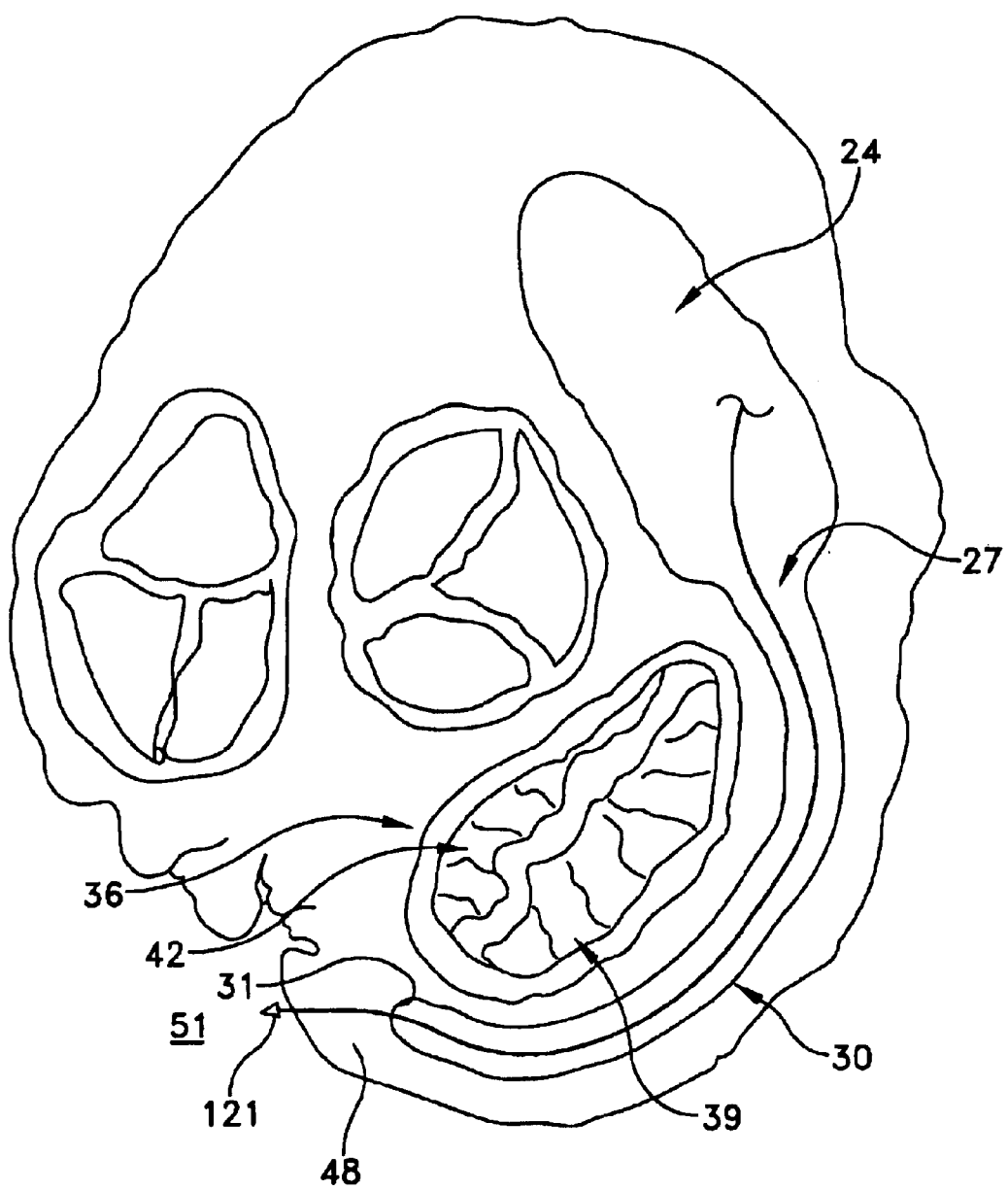
FIGS. 4–10 are a series of views illustrating use of the system of FIG. 3 to reduce mitral regurgitation.

Cinching device 106 comprises a flexible body or filament 124 having a distal end 127 and a proximal end 130. In the case where central lumen 136 extends from distal end 127 to proximal end 130, central lumen 136 would preferably collapse on itself when guidewire 103 is removed or a portion of guidewire 103 would remain within central lumen 136 to prevent blood from the right atrium from bleeding into the pericardial space 51. See FIG. 4. A distal anchor 139 is disposed at the distal end 127 of flexible body 124 and is preferably constructed from or covered with a material which promotes blood clotting to seal the hole created by the tip of guidewire 103 and distal end 127 of flexible body 124. A proximal anchor 142 is disposed at the proximal end 130 of flexible body 124. Proximal anchor 142 preferably comprises a plurality of radial projections 145 formed on flexible body 124 and a head 146 having a central opening 147 therein. Head 146 is intended to "ratchet" over radial projections 145 so as to be adjustable along flexible body 124. More particularly, by ratcheting head 146 distally or proximally along radial projections 145, the length of filament extending between distal anchor 139 and proximal anchor 142 may be shortened or lengthened as desired. Head 146 also includes one or more holes H for permitting blood to flow past head 146 when the cinching device is deployed in the body.

Delivery catheter 109 comprises a flexible body 148 having a distal end 151 and a proximal end 154. A central lumen 157 extends down the length of flexible body 148.

System 100 may be used as follows to reduce mitral regurgitation.

First, using devices and method currently well known to interventional cardiologists any commercially available delivery catheter is passed down the jugular vein 18 (or the left subclavian vein 15) of a patient, down superior vena cava 9, through right atrium 24 of the heart, and then into coronary sinus 30. When the tip of the commercially available delivery catheter is located at or near the entrance of the AIV, guidewire 103 is passed down the center of catheter 109. It will be appreciated that as the commercially available delivery catheter and flexible guidewire 103 are passed down coronary sinus 30, the catheter and guidewire will tend to assume the natural curved shape of the coronary sinus, due to the flexible nature of the catheter and guidewire. Then the guidewire's sharp tip 121 is pushed through the end wall 31 of the coronary sinus, across the intervening tissue 48 and into pericardial space 51 and the commercially available delivery catheter is removed leaving the flexible guidewire 103 in place. See FIG. 4.

Figure 5:
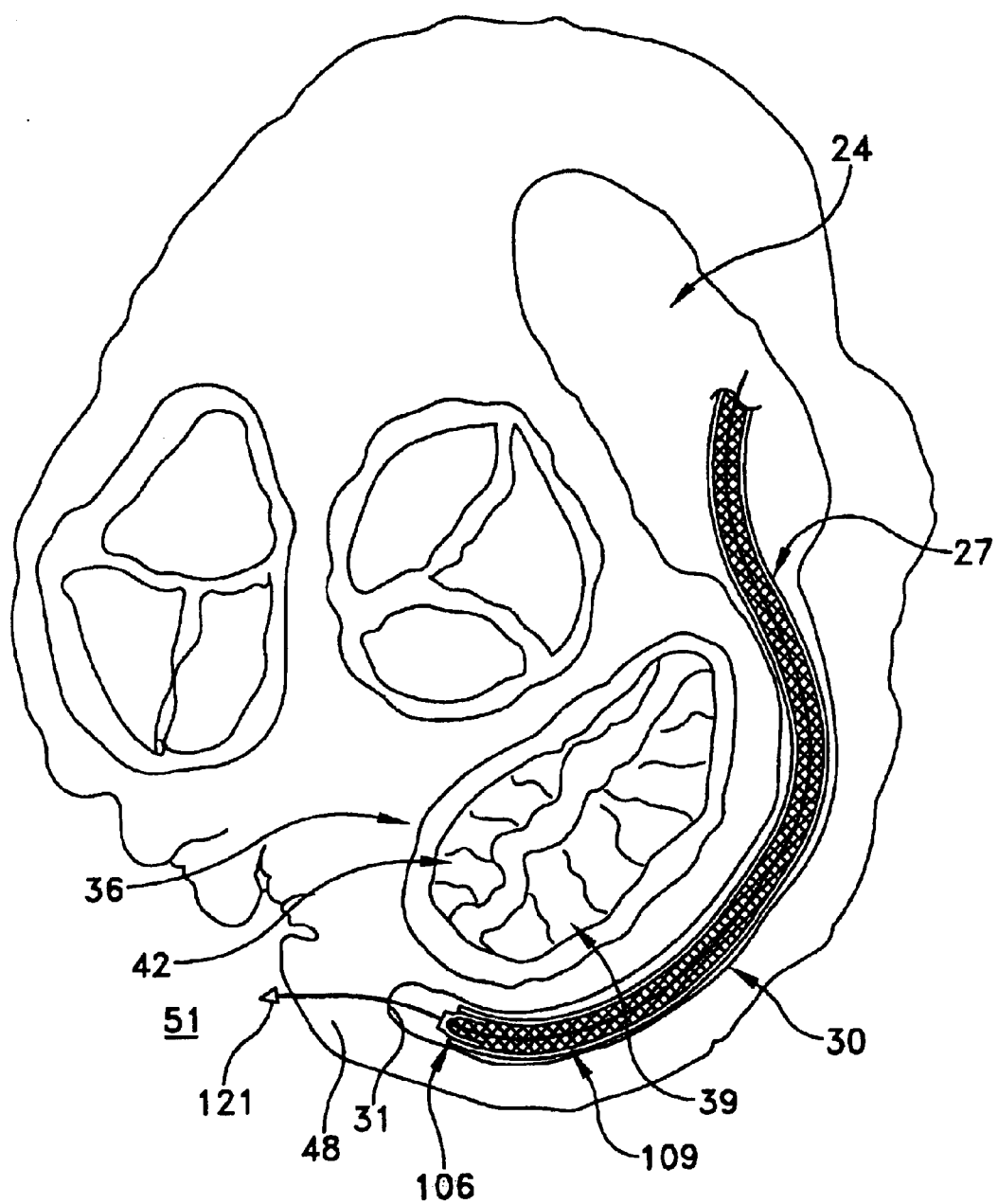

Next, cinching device 106 and delivery catheter 109 are passed down over the guidewire 103 until the distal end of the delivery catheter is positioned in coronary sinus 30. See FIG. 5. More particularly, cinching device 106, with its distal anchor 139 and head 146 of proximal anchor 142 in folded back positions, is loaded into the interior lumen 157 of delivery catheter 109, and then the assembly is fit over guidewire 103, with guidewire 103 being received in central lumen 136 of cinching device 106. Cinching device 106 and delivery catheter 109 are passed down guidewire 103, together, in this position. Again, it will be appreciated that as the cinching device 106 and flexible delivery catheter 109 pass down the coronary sinus, the cinching device and delivery catheter will tend to assume the natural curved shape of the coronary sinus, due to the flexible natures of the cinching device and the delivery catheter.

Figure 6:
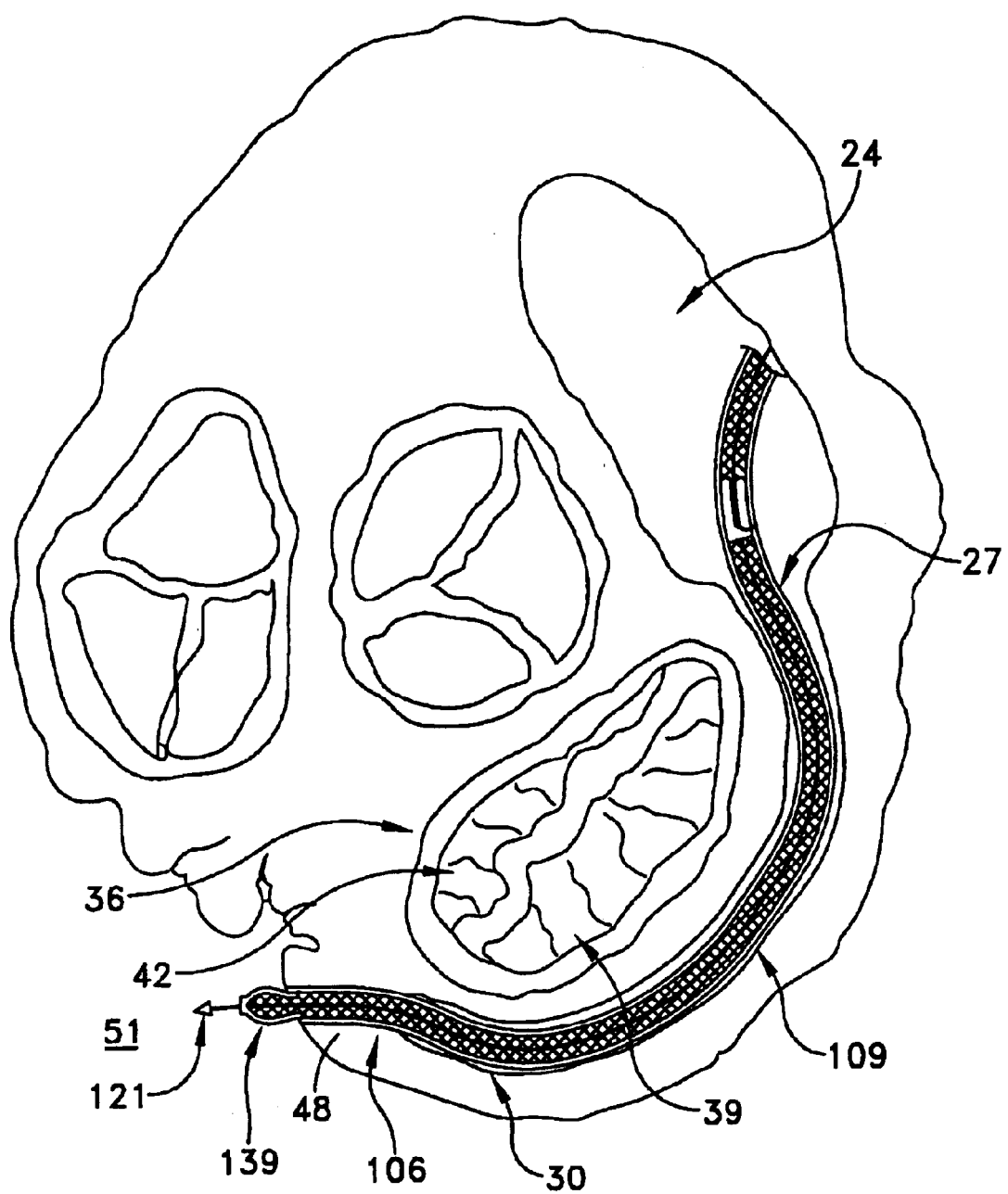
Figure 7:
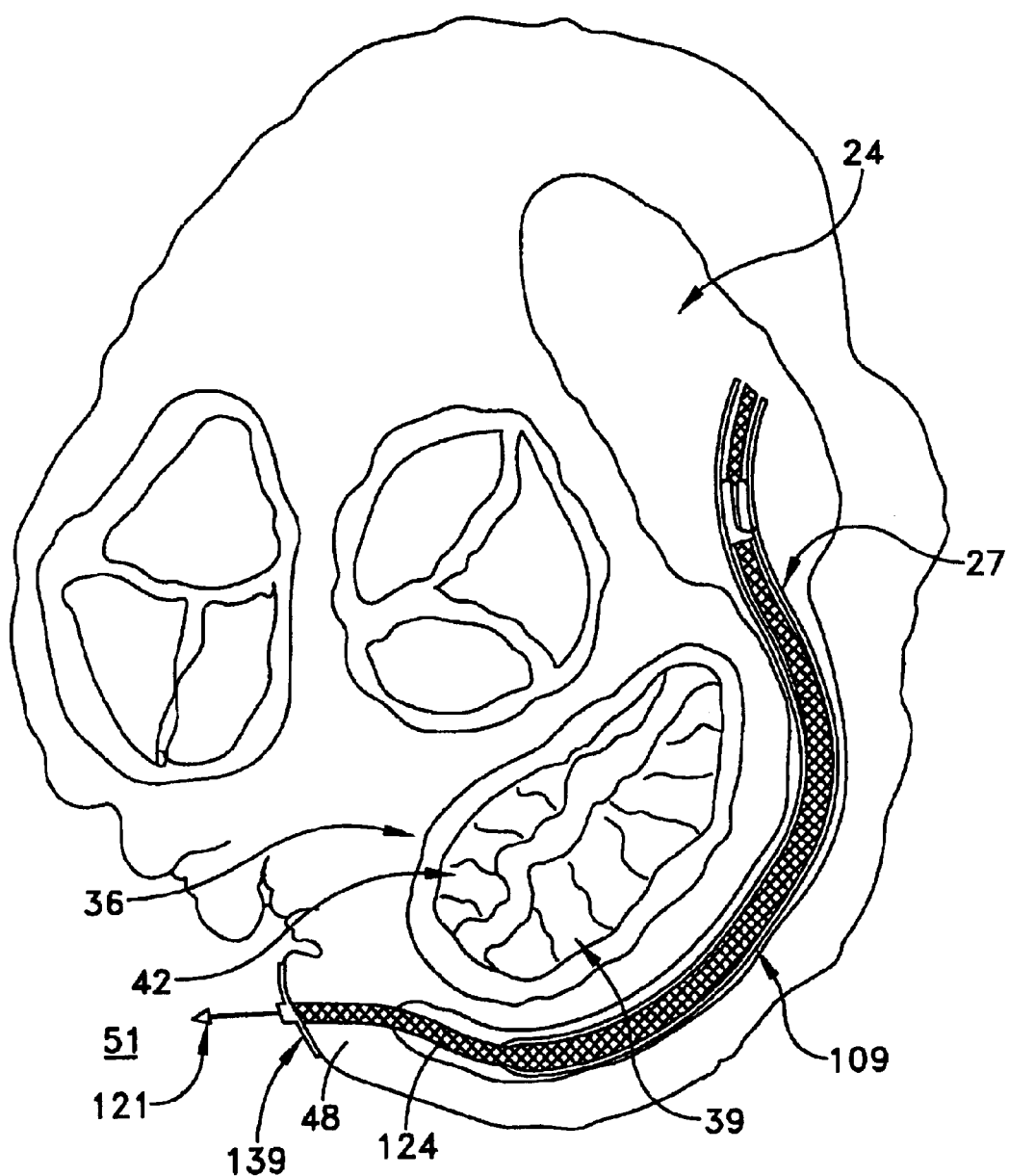

Then, with the distal end 151 of delivery catheter 109 positioned at the far end 31 of the coronary sinus, the distal end of cinching device 106 is advanced forward, through intervening tissue 48, until it enters pericardial space 51. See FIG. 6. At this point the distal anchor 139 of cinching device 106 deploys. See FIG. 7.

Figure 8:
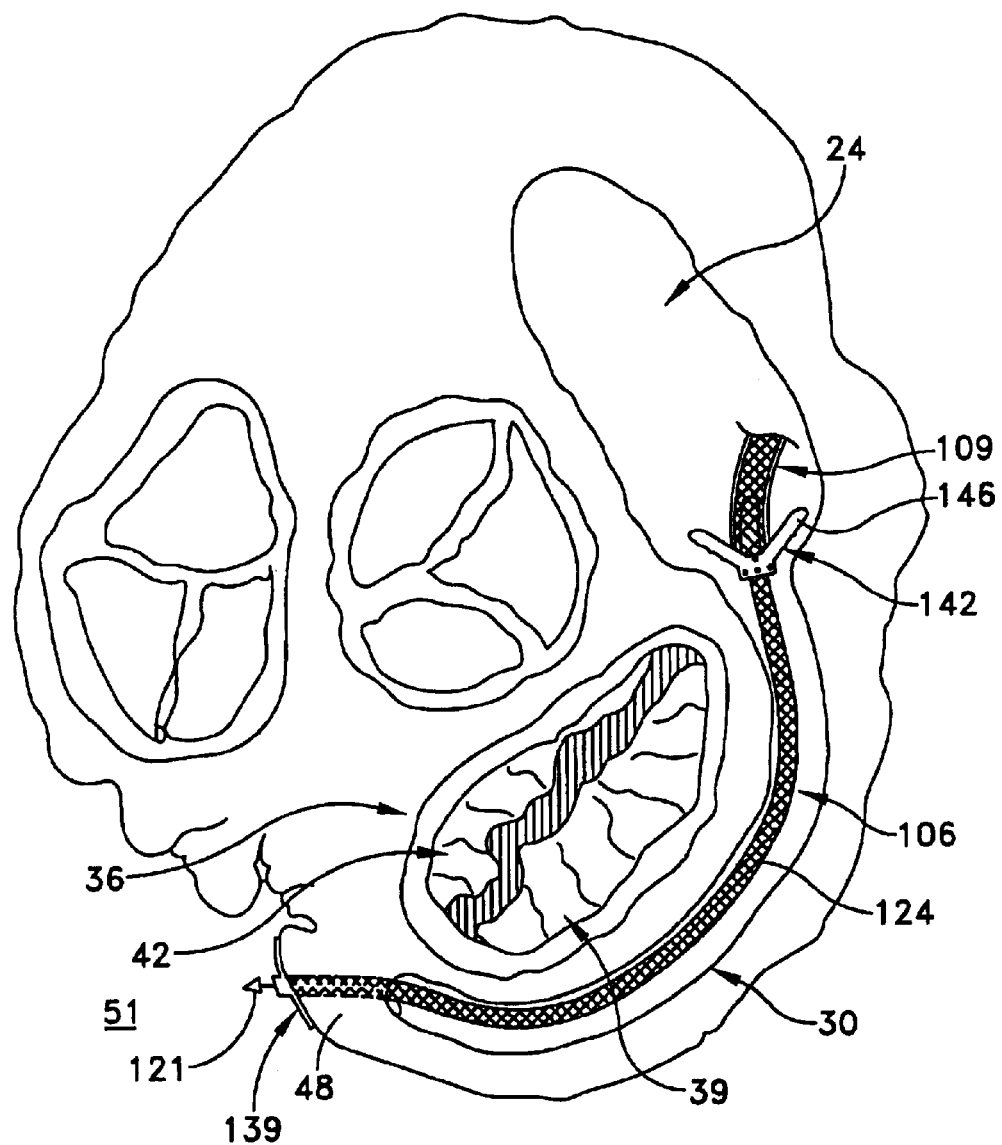

Next, delivery catheter 109 is withdrawn proximally until it's distal end is disposed proximally of the cinching device's proximal anchor 142, whereupon head 146 of the proximal anchor 142 will unfold. See FIG. 8.

Figure 9:
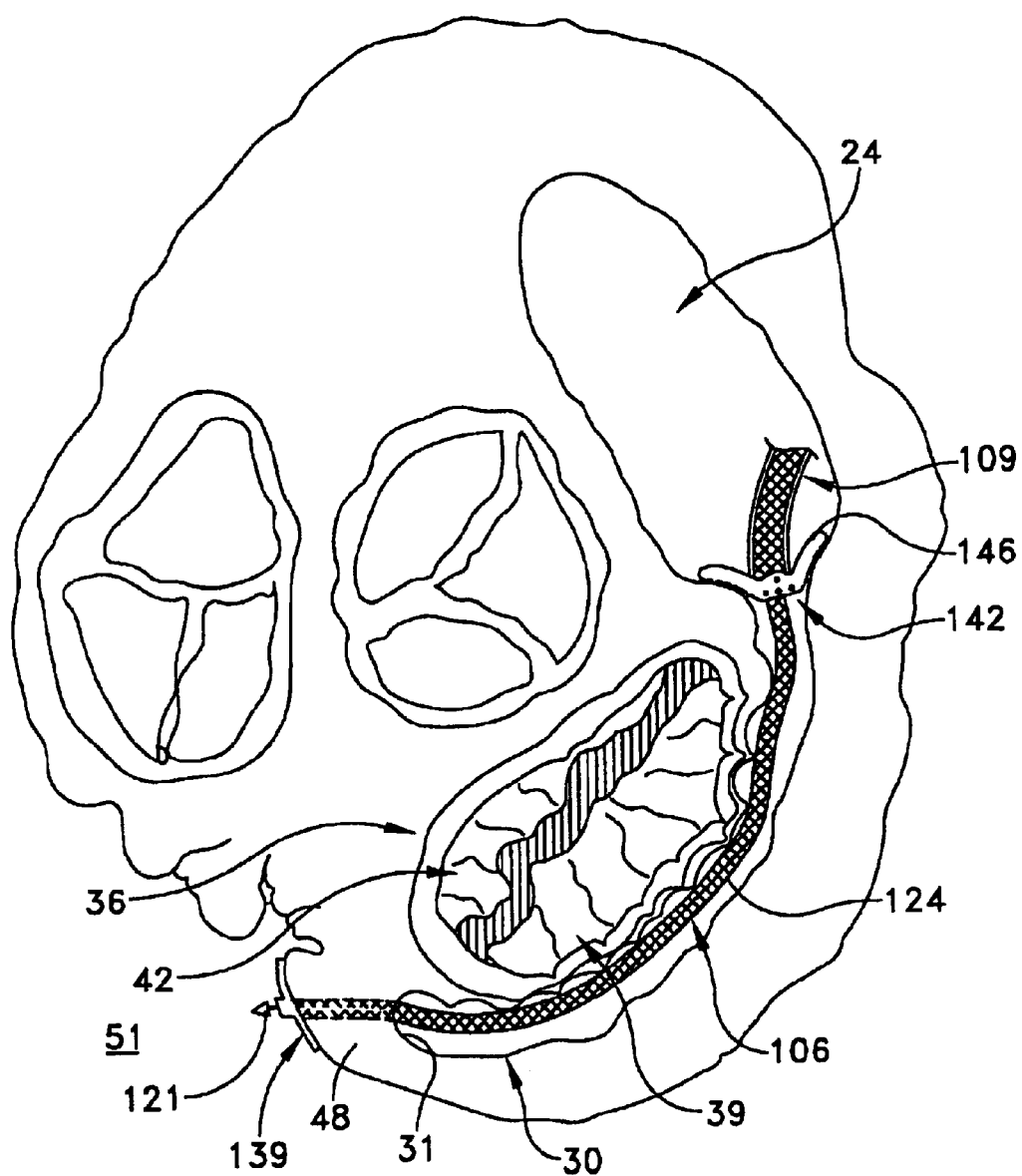

Next, the cinching device's head 146 is advanced distally, over ratcheting projections 145, until head 146 engages the coronary ostium 27. Then the proximal end of flexible body 124 is withdrawn proximally, causing the distance between distal anchor 139 and proximal anchor 142 to be reduced, whereby to cause at least a portion of coronary sinus 30 to assume a more straight configuration adjacent to the posterior annulus of mitral valve 36. See FIG. 9. This action causes the posterior annulus of mitral valve 36 to be forced anteriorly, whereby the mitral valve's posterior leaflet 39 will also move anteriorly so as to improve mitral valve leaflet coaptation and thereby reduce (or completely eliminate) mitral valve regurgitation. In this respect it should be appreciated that the posterior annulus may be shifted anteriorly so as to achieve, or to attempt to achieve to the extent anatomically possible, leaflet-to-leaflet engagement or leaflet-to-annulus engagement (e.g., where a leaflet may be tethered due to left ventricular distortion). Both of these types of engagement, or targeted engagement, are intended to be encompassed by the terms "improved leaflet coaptation" and/or "increased leaflet coaptation" and the like. Using standard visualization means (e.g. echocardiography or fluoroscopy), the degree of cinching is adjusted (i.e., either tighter or looser) so as to reduce (or completely eliminate) regurgitation in mitral valve 36.

It should be appreciated that when the cinching device's head 146 is in engagement with coronary ostium 27, blood will be free to flow into the coronary ostium due to the presence of holes H in head 146.

At this point the cinching device 106 is locked in position.

Figure 10:
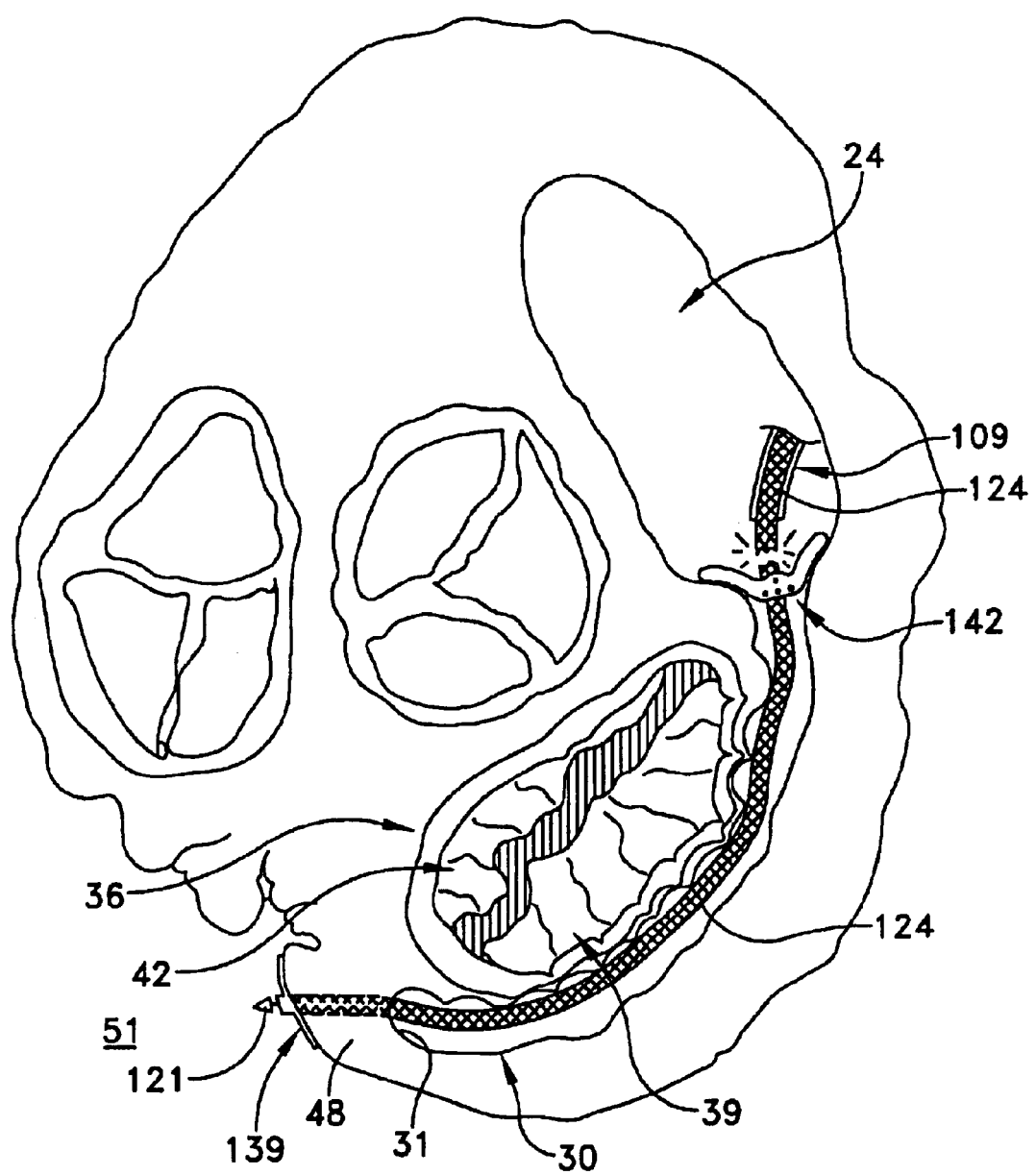

System 100 is left in this position until it is no longer needed. In some cases this may mean that system 100 is left in position for a period of a few hours, days or weeks; in other cases system 100 may be substantially permanent. If system 100 is to be left in position, the proximal end of flexible body 124 may be cut away and removed. See FIG. 10. This may be done with an instrument advanced down delivery catheter 109. Then delivery catheter 109 is removed from the patient.

Thus it will be seen that with the present invention, cinching device 106 is positioned in the normally curved portion of the coronary sinus adjacent to the mitral valve's posterior leaflet, with its distal anchor 139 located in pericardial space 51 and its proximal anchor 142 located at the coronary ostium 27. By properly cinching the length of filament 124 between these two anchors, cinching device 106 will cause at least a portion of the coronary sinus to assume a more straight configuration adjacent to the posterior leaflet of the mitral valve. This action will in turn drive the posterior annulus of the mitral valve anteriorly, so as to improve leaflet coaptation and thereby reduce mitral regurgitation. Thus, by inserting the cinching device 106 into the coronary sinus adjacent to the posterior leaflet of the mitral valve and thereafter cinching it down as appropriate, the annulus of the mitral valve is effectively manipulated so that it will assume an increased radius of curvature.

It has also been found that by inserting the cinching device into the coronary sinus adjacent to the posterior leaflet of the mitral valve, the left ventricle may also be remodeled so as to help alleviate congestive heart failure.

Figure 11:
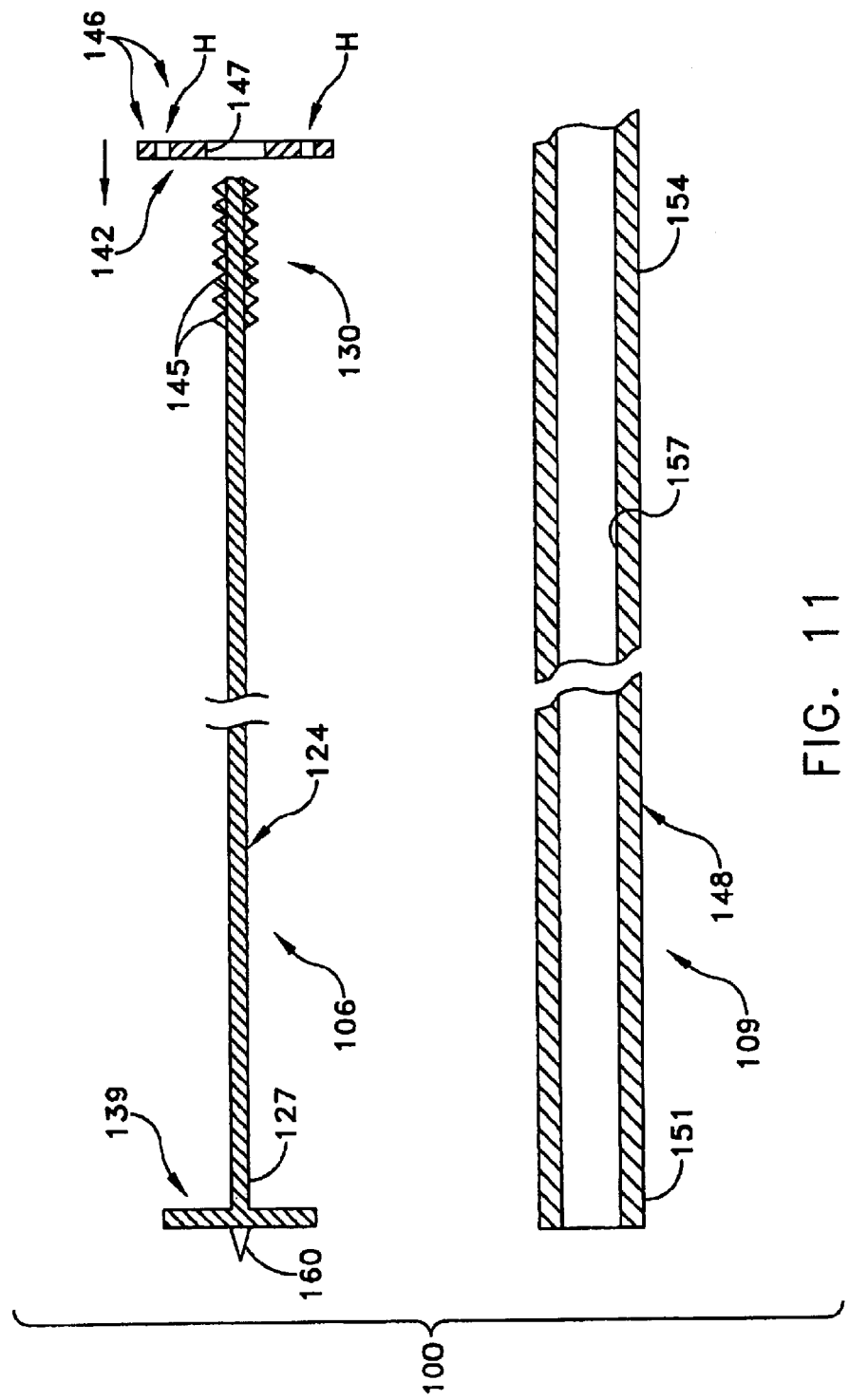
FIG. 11 is a schematic view showing another embodiment of apparatus formed in accordance with the present invention.

In an alternative embodiment of the invention, the delivery catheter 109 is itself guided into coronary sinus 30 without the use of guidewire 103, and the distal end of cinching device 106 is used to open a path through intervening tissue 48 and into pericardial space 51. In this form of the invention, guidewire 103 may be omitted entirely, and the central lumen 136 in cinching device 106 may also be omitted. However, the distal end of cinching device 106 preferably has a trocar device to help open a path through intervening tissue 48. See, for example, FIG. 11, where system 100 is shown comprising cinching device 106 and delivery catheter 109, and further wherein cinching device 106 comprises a distal trocar 160 to open a path through intervening tissue 48 and into pericardial space 51.

Figure 12:
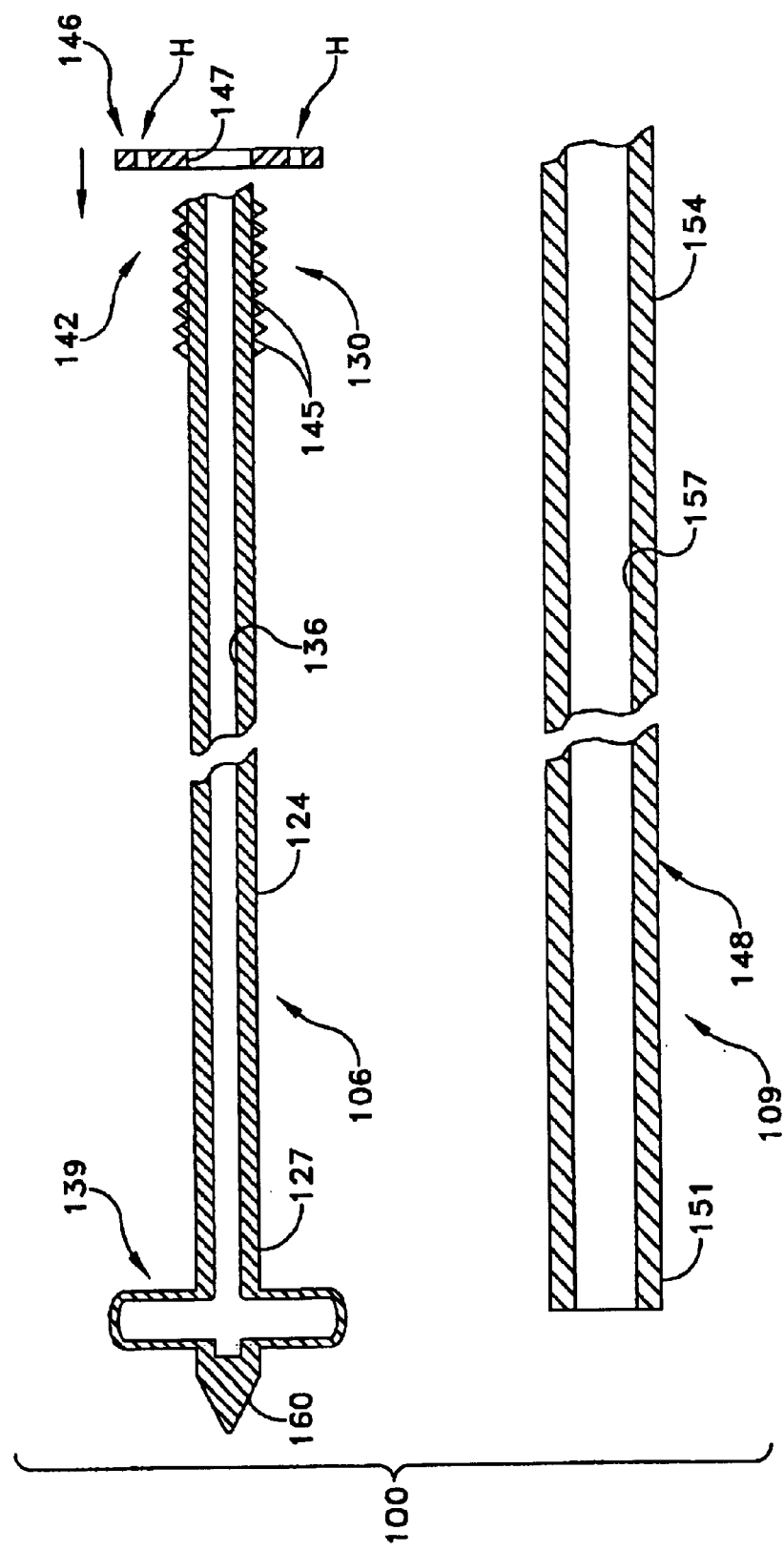
FIG. 12 is a schematic view showing still another embodiment of apparatus formed in accordance with the present invention.

And in another alternative embodiment of the invention, the cinching device's distal anchor 139 and/or its proximal anchor 142 may be replaced with an inflatable balloon anchor. In this case delivery catheter 109 may be adapted so that it is itself guided into coronary sinus 30 without the use of guidewire 103, and the central lumen 136 of cinching device 106 may be used as an inflation lumen. See, for example, FIG. 12, where system 100 is shown comprising cinching device 106 and delivery catheter 109, and further wherein cinching device 106 comprises a distal anchor 139 comprising an inflatable balloon and a distal trocar 160 to open a path through intervening tissue 48 and into pericardial space 51. Central lumen 136 allows fluid to be delivered to and removed from the inflatable balloon, whereby to inflate or deflate the balloon on command.

Figure 9A:
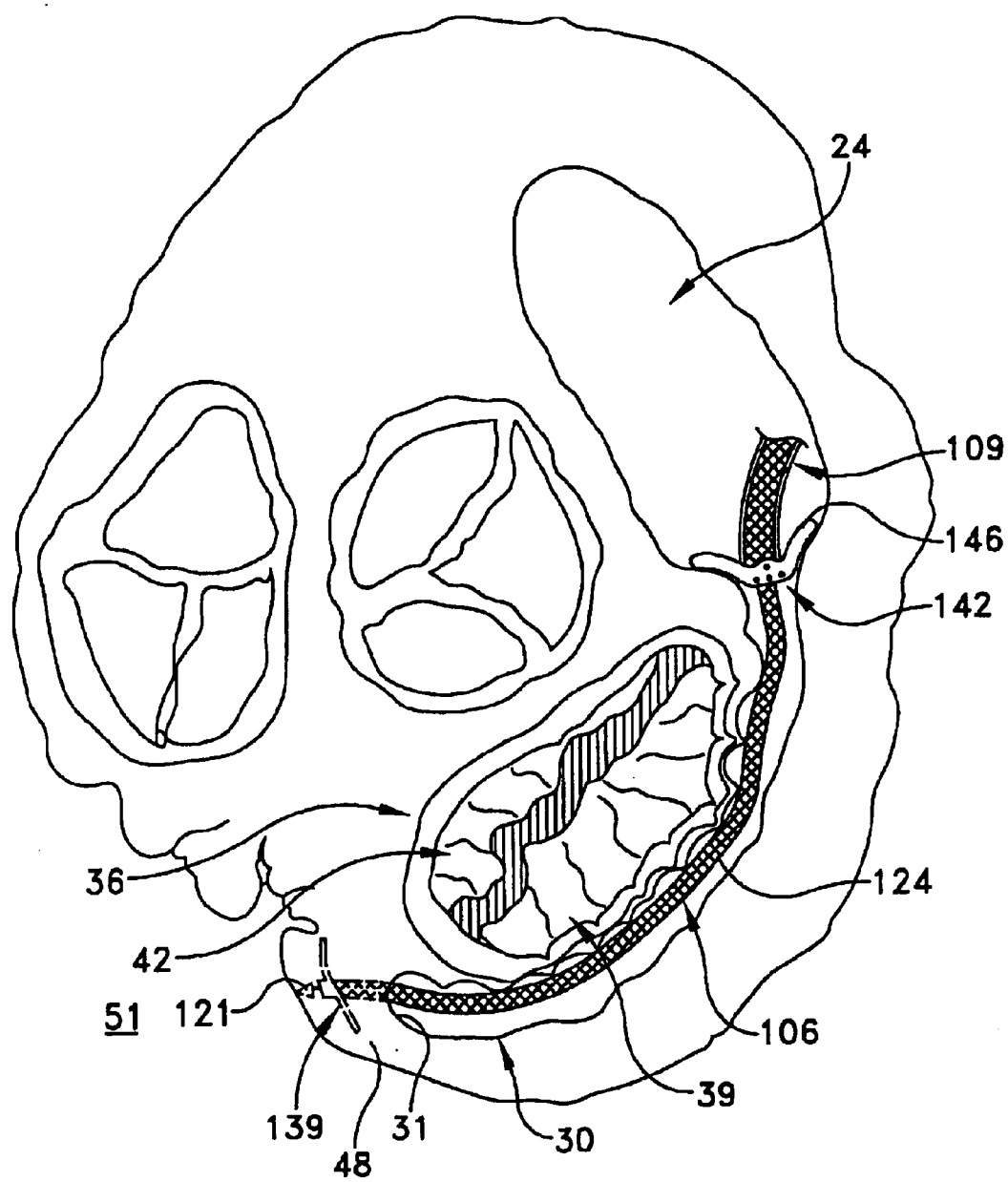
Figure 9B:
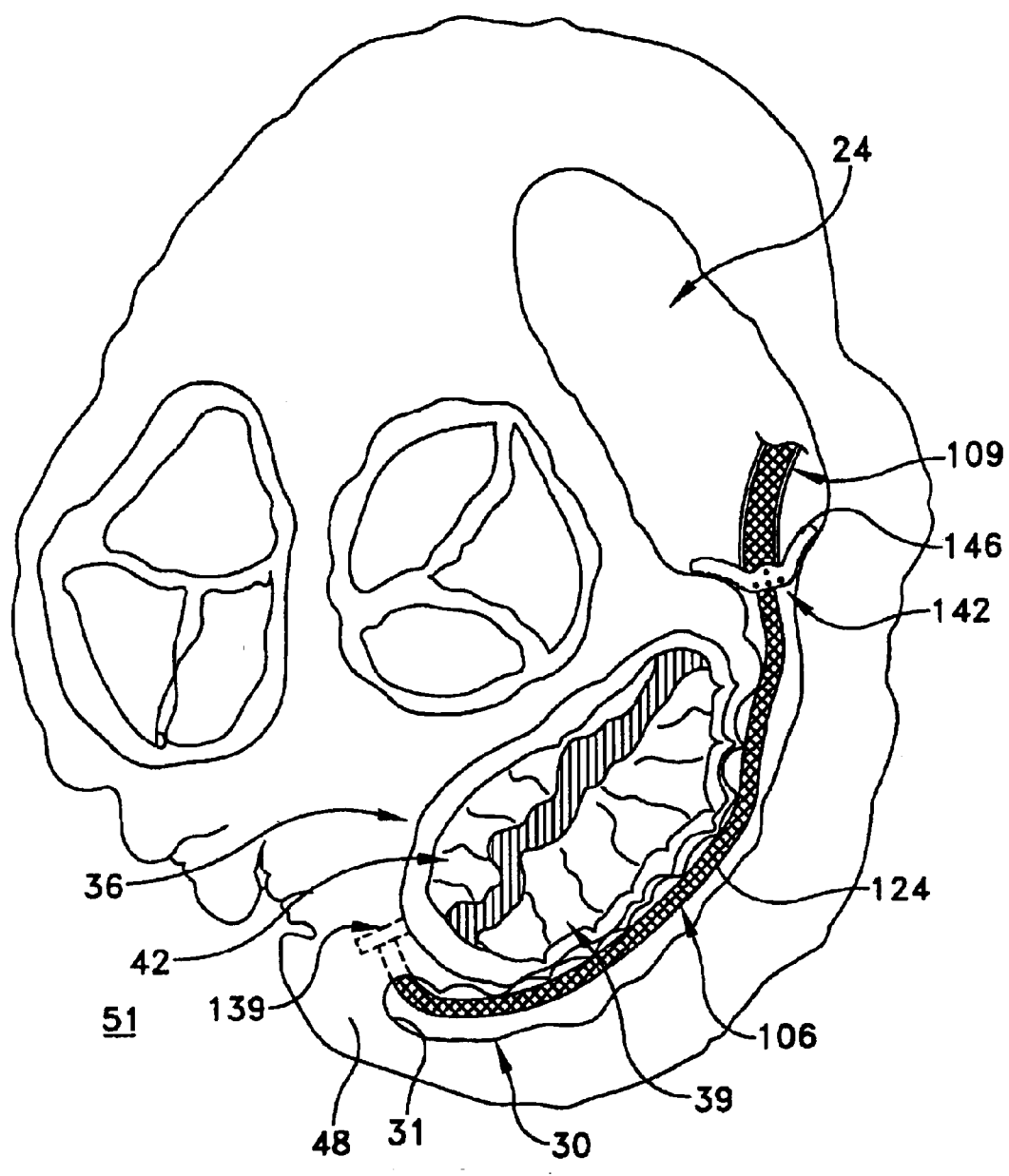

In the procedures described above, the distal end of cinching device 106 (and, depending on the embodiment, the distal end of guidewire 103) is described as penetrating all the way through the intervening tissue 48 and into pericardial space 51, so that the distal anchor 139 can be set into pericardial space 51 and bear against the exterior of intervening tissue 48. This arrangement is generally preferred, since it allows greater separation between distal anchor 139 and proximal anchor 142, and since it allows a strong anchoring arrangement highly resistant to slippage. However, if desired, and referring to FIG. 9A, it is also possible to set distal anchor 139 into intervening tissue 48 at a location to the interior of pericardial space 51. In addition, and referring to FIG. 9B, it is possible to set distal anchor 139 through the myocardium tissue, i.e. intervening tissue 48, and into the left ventricle.

Similarly, in the procedures described above, the proximal anchor 142 is described as being set against coronary ostium 27. Again, this arrangement is generally preferred since it allows good anchor separation and it allows a strong anchoring arrangement highly resistant to slippage. However, if desired, it is also possible to set proximal anchor 142 at other locations.

The procedures described above relate to effecting changes in left atrial geometry using access obtained via the coronary sinus or other cardiac vein. Such procedures might also be performed using access obtained via the circumflex coronary artery. In addition, a similar approach could be used to perform procedures on the tricuspid valve.

It will be understood that the particular devices and methods embodying the invention are shown by way of illustration only and not as limitations of the invention. The principles and features of this invention may be employed in various and numerous embodiments without departing from the scope of the invention.

What is claimed is:

1. A method for reducing mitral regurgitation, said method comprising the steps of:
    providing a cinching device comprising a distal anchor, a proximal anchor, and a flexible body extending therebetween, said distal anchor configured for positioning distal to the distal end of the coronary sinus and the proximal anchor configured for positioning at the coronary ostium, with said flexible body configured to extend through the coronary sinus between said distal anchor and said proximal anchor, and further wherein said proximal anchor is configured for ratcheting action relative to said flexible body, whereby the length of said flexible body between said distal anchor and said proximal anchor may be reduced;
    positioning said distal anchor distal to the distal end of the coronary sinus and penetrating through the distal end wall of the coronary sinus and positioning said proximal anchor at the coronary ostium, with said flexible body extending through the coronary sinus between said distal anchor and said proximal anchor; and
    cinching said flexible body so as to reduce the length of said flexible body between said distal anchor and said proximal anchor, whereby a force is exerted on the posterior annulus so as to reduce mitral regurgitation.

2. A method according to claim 1 wherein said distal anchor is set in the pericardial space adjacent to the distal end of the coronary sinus.

3. A method according to claim 1 wherein said distal anchor is set in the intervening tissue located between the pericardial space and the distal end of the coronary sinus.

4. A method according to claim 1 wherein said proximal anchor comprises a plurality of radial projections formed on said flexible body and a head having a central opening therein, the size and construction of said radial projections and said opening being coordinated so as to enable a ratcheting action between said flexible body and said head, and further wherein cinching said flexible body is achieved by moving said head relative to said flexible body.

5. A method according to claim 4 wherein said head has a plurality of openings therein so as to pass blood therethrough.

6. A method according to claim 1 wherein said cinching device is carried to the coronary sinus inside a delivery catheter.

7. A method according to claim 1 wherein said cinching device is carried to the coronary sinus over a guidewire.

8. A method according to claim 1 wherein said distal anchor is set through the myocardium tissue and into the left ventricle adjacent to the distal end of the coronary sinus.

9. A method for reducing mitral regurgitation, said method comprising the steps of:
    providing a cinching device comprising a distal anchor, a proximal anchor, and a flexible body extending therebetween, said distal anchor configured for positioning distal to the distal end of the coronary sinus and the proximal anchor configured for positioning at the coronary ostium, with said flexible body configured to extend through the coronary sinus between said distal anchor and said proximal anchor, and further wherein said proximal anchor is configured for ratcheting action relative to said flexible body, whereby the length of said flexible body between said distal anchor and said proximal anchor may be reduced;
    positioning said distal anchor distal to the distal end of the coronary sinus and positioning said proximal anchor at the coronary ostium, with said flexible body extending through the coronary sinus between said distal anchor and said proximal anchor; and
    cinching said flexible body so as to reduce the length of said flexible body between said distal anchor and said proximal anchor, whereby a force is exerted on the posterior annulus so as to reduce mitral regurgitation;
    wherein said distal anchor is set in the pericardial space adjacent to the distal end of the coronary sinus.

10. A method for reducing mitral regurgitation, said method comprising the steps of:
    providing a cinching device comprising a distal anchor, a proximal anchor, and a flexible body extending therebetween, said distal anchor configured for positioning distal to the distal end of the coronary sinus and the proximal anchor configured for positioning at the coronary ostium, with said flexible body configured to extend through the coronary sinus between said distal anchor and said proximal anchor, and further wherein said proximal anchor is configured for ratcheting action relative to said flexible body, whereby the length of said flexible body between said distal anchor and said proximal anchor may be reduced;
    positioning said distal anchor distal to the distal end of the coronary sinus and positioning said proximal anchor at the coronary ostium, with said flexible body extending through the coronary sinus between said distal anchor and said proximal anchor; and
    cinching said flexible body so as to reduce the length of said flexible body between said distal anchor and said proximal anchor, whereby a force is exerted on the posterior annulus so as to reduce mitral regurgitation;
    wherein said proximal anchor comprises a plurality of radial projections formed on said flexible body and a head having a central opening therein, the size and construction of said radial projections and said opening being coordinated so as to enable a ratcheting action between said flexible body and said head, and further wherein cinching said flexible body is achieved by moving said head relative to said flexible body; and wherein said head has a plurality of openings therein so as to pass blood therethrough.

11. A method for reducing mitral regurgitation, said method comprising the steps of:

providing a cinching device comprising a distal anchor, a proximal anchor, and a flexible body extending therebetween, said distal anchor configured for positioning distal to the distal end of the coronary sinus and the proximal anchor configured for positioning at the coronary ostium, with said flexible body configured to extend through the coronary sinus between said distal anchor and said proximal anchor, and further wherein said proximal anchor is configured for ratcheting action relative to said flexible body, whereby the length of said flexible body between said distal anchor and said proximal anchor may be reduced;

positioning said distal anchor distal to the distal end of the coronary sinus and positioning said proximal anchor at the coronary ostium, with said flexible body extending through the coronary sinus between said distal anchor and said proximal anchor; and cinching said flexible body so as to reduce the length of said flexible body between said distal anchor and said proximal anchor, whereby a force is exerted on the posterior annulus so as to reduce mitral regurgitation;

wherein said distal anchor is set through the myocardium tissue and into the left ventricle adjacent to the distal end of the coronary sinus.

* * * * *